(12) United States Patent
Furuichi et al.

(10) Patent No.: US 10,733,753 B2
(45) Date of Patent: Aug. 4, 2020

(54) IMAGE DISPLAY DEVICE AND ITS CONTROL METHOD, X-RAY OPAQUE MARKER DETECTION METHOD

(71) Applicant: TERUMO KABUSHIKI KAISHA, Shibuya-ku, Tokyo (JP)

(72) Inventors: Junya Furuichi, Hadano (JP); Isao Mori, Chofu (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 641 days.

(21) Appl. No.: 15/412,550

(22) Filed: Jan. 23, 2017

(65) Prior Publication Data

US 2017/0213358 A1   Jul. 27, 2017

(30) Foreign Application Priority Data

Jan. 26, 2016   (JP) .................. 2016-012769

(51) Int. Cl.
*A61B 5/05* (2006.01)
*G06T 7/73* (2017.01)
(Continued)

(52) U.S. Cl.
CPC ............. *G06T 7/73* (2017.01); *A61B 6/032* (2013.01); *A61B 6/12* (2013.01); *A61B 6/4417* (2013.01); *A61B 6/463* (2013.01); *A61B 6/504* (2013.01); *A61B 6/541* (2013.01); *A61B 8/12* (2013.01); *A61B 8/463* (2013.01); *A61B 90/39* (2016.02); *A61B 5/0035* (2013.01); *A61B 5/0066* (2013.01); *A61B 5/0084* (2013.01); *A61B 5/064* (2013.01); *A61B 6/481* (2013.01); *A61B 8/0891* (2013.01); *A61B 8/4245* (2013.01); *A61B 8/4416* (2013.01); *A61B 2090/3966* (2016.02); *G06T 2207/10081* (2013.01);
(Continued)

(58) Field of Classification Search
CPC ....... A61B 6/481; A61B 6/4417; A61B 5/064; A61B 5/0035; A61B 5/0084; A61B 5/0066; A61B 8/4416; A61B 8/4245; A61B 8/0891
See application file for complete search history.

(56) References Cited

U.S. PATENT DOCUMENTS 7,930,014 B2   4/2011   Huennekens et al.
2007/0123771 A1   5/2007   Redel et al.
(Continued)

FOREIGN PATENT DOCUMENTS

EP   2873371 A1   5/2015

OTHER PUBLICATIONS

The extended European Search Report dated Jun. 6, 2017, by the European Patent Office in corresponding European Patent Application No. 17152374.9 (8 pgs).

*Primary Examiner* — Mallika D Fairchild
(74) *Attorney, Agent, or Firm* — Buchanan Ingersoll & Rooney PC (57) ABSTRACT

A radiopaque marker detection method of detecting the radiopaque marker disposed in a probe on multiple X-ray images captured while the probe for acquiring the tomographic image moves in an axial direction of a catheter, a position of the radiopaque marker disposed in the probe on each of the multiple X-ray images captured during the movement of the probe is detected from the X-ray images captured during a predetermined period before the probe starts to move, by extracting a line extending along the probe and using the extracted line.

20 Claims, 9 Drawing Sheets (51) Int. Cl.

| | | |
|---|---|---|
| *A61B 6/12* | (2006.01) | |
| *A61B 6/00* | (2006.01) | |
| *A61B 6/03* | (2006.01) | |
| *A61B 8/12* | (2006.01) | |
| *A61B 8/00* | (2006.01) | |
| *A61B 90/00* | (2016.01) | |
| *A61B 8/08* | (2006.01) | |
| *A61B 5/00* | (2006.01) | |
| *A61B 5/06* | (2006.01) | |

(52) U.S. Cl.
CPC ............... *G06T 2207/10132* (2013.01); *G06T 2207/30101* (2013.01); *G06T 2207/30204* (2013.01); *G06T 2210/41* (2013.01)

(56) References Cited

U.S. PATENT DOCUMENTS

| | | |
|---|---|---|
| 2012/0059253 A1 | 3/2012 | Wang et al. |
| 2014/0270436 A1 | 9/2014 | Dascal et al. |
| 2015/0131886 A1 | 5/2015 | Aben et al. |

IMAGE DISPLAY DEVICE AND ITS CONTROL METHOD, X-RAY OPAQUE MARKER DETECTION METHOD

CROSS-REFERENCES TO RELATED APPLICATIONS

This application claims priority to Japanese Application No. 2016-012769 filed on Jan. 26, 2016, the entire content of which is incorporated herein by reference.

TECHNICAL FIELD

The present disclosure relates to detecting a position of a catheter for generating a tomographic image of a living body tissue.

BACKGROUND ART

Endovascular treatment can be performed using a high-performance catheter such as a balloon catheter and a stent. An intravascular ultrasound (IVUS) apparatus has been used for preoperative diagnosis or for confirmation of postoperative results. In addition, instead of the IVUS apparatus, an optical coherence tomography (OCT) apparatus has been used. As an improved OCT apparatus, a swept-source optical coherence tomography (SS-OCT) apparatus utilizing wavelength sweeping has been used. A vascular diagnosis apparatus which can acquire a tomographic image, such as the IVUS apparatus and the OCT apparatus, is used in order to obtain more detailed information of a lesion site confirmed by an X-ray apparatus, for example, a stenosed rate in blood vessels, presence of plaques in bifurcated blood vessels, or calcification distribution.

In a case where a physician determines that treatment is required, the physician observes a blood vessel tomographic image obtained by the above-described vascular diagnosis apparatus, thereby determining treatment details, for example, such as where to locate an edge position of the stent. In a case of treating a determined treatment site, the physician performs treatment for installing a balloon or the stent while observing an X-ray image (angiography) obtained by the X-ray apparatus. Therefore, it can be a very important factor for the treatment to understand that an installation position of the balloon or the stent which is determined after the physician confirms the blood vessel tomographic image corresponds to any position on the X-ray image.

As described above, it can be important for the endovascular treatment to recognize a positional relationship between the obtained blood vessel tomographic image and the X-ray image. However, the vascular diagnosis apparatus and the X-ray apparatus are configured to include respectively different modalities. Accordingly, a physician needs to perform treatment by estimating a position on the X-ray image corresponding to the confirmed blood vessel tomographic image, while relying on a landmark, for example, such as a bifurcated position.

In order to improve accuracy in estimating the position on the X-ray image corresponding to the blood vessel tomographic image as described above, a blood vessel tomographic image apparatus is present which displays the X-ray image after capturing the X-ray image when the blood vessel tomographic image is acquired and synchronizing the X-ray image with the blood vessel tomographic image. In general, a radiopaque marker is installed in the vicinity of a sensor in a catheter connected to the blood vessel tomographic image apparatus. The blood vessel tomographic image and the X-ray image are displayed in synchronization with each other, thereby improving the above-described estimation accuracy. If this function is used, the blood vessel tomographic image and the position of the radiopaque marker on the X-ray image can be visualized through one-to-one correspondence.

Furthermore, in recent years, a technique has been developed which further improves visibility by automatically detecting and highlighting the radiopaque marker from the X-ray image (refer to U.S. Pat. No. 7,930,014). However, a position of the blood vessel displayed on the X-ray image varies due to influence of heartbeats or breathing with the lapse of time. Furthermore, there is a big individual difference in the number of bifurcated human blood vessels or a configuration the bifurcated blood vessels. In some cases, many bifurcated blood vessels are present around a target blood vessel. For these reasons, an automatic detection rate of the radiopaque marker on the X-ray image is not satisfactorily high.

SUMMARY

The present disclosure is made in view of the above-described problems, and an object thereof is to improve a detection rate of the radiopaque marker on the X-ray image acquired while the tomographic image is acquired.

According to an aspect of the present disclosure, in order to achieve the above-described object, an X-ray marker detection device includes an image display device that displays multiple tomographic images acquired while moving a probe in an axial direction of a catheter and multiple X-ray images captured during the movement of the probe. The image display device includes extraction means for extracting a line extending along the probe from the X-ray image captured during a predetermined period before the probe starts to move, detection means for detecting a position of a radiopaque marker disposed in the probe on each of the multiple X-ray images captured during the movement of the probe, by using the line extracted by the extraction means, and display control means for synchronously displaying the multiple X-ray images and the multiple tomographic images so as to specify the position of the radiopaque marker detected by the detection means, when the X-ray image is displayed in the synchronous display.

In addition, according to another aspect of the present disclosure, a radiopaque marker detection method is disclosed of detecting a radiopaque marker disposed in a probe on multiple X-ray images captured while the probe for acquiring a tomographic image moves in an axial direction of a catheter. The radiopaque marker detection method includes an extraction process of extracting a line extending along the probe from the X-ray image captured during a predetermined period before the probe starts to move, and a detection process of detecting a position of a radiopaque marker disposed in the probe on each of the multiple X-ray images captured during the movement of the probe, by using the line extracted during the extraction process.

According to the present disclosure, an X-ray image captured before acquiring a tomographic image is used. In this manner, it is possible to improve a detection rate of a radiopaque marker present on the X-ray image acquired while the tomographic image is acquired.

DETAILED DESCRIPTION

Hereinafter, an example of a preferred embodiment according to the present disclosure will be described with reference to the accompanying drawings.

Figure 1:
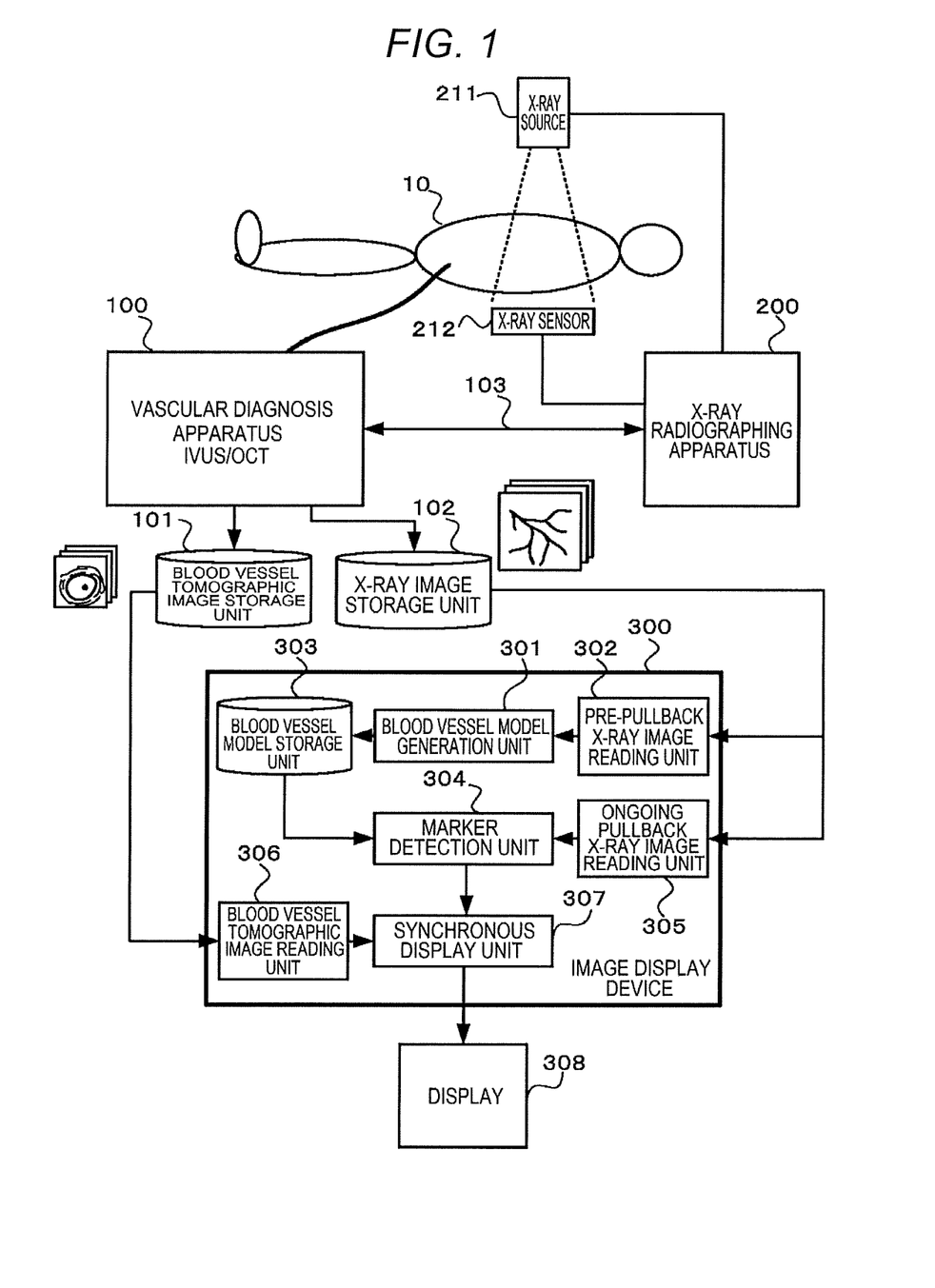
FIG. 1 is a view for describing a configuration of a display system according to an embodiment.

FIG. 1 is a view illustrating a configuration example of a display system, which can realize synchronous display of a blood vessel tomographic image and an X-ray image (angiographic image). In FIG. 1, a vascular diagnosis apparatus 100 functioning as a tomographic image acquisition unit acquires a vascular tomographic image by using an intravascular ultrasound (IVUS) method or an optical coherence tomography (OCT) method. For example, in order to capture the vascular tomographic image around a heart of a patient 10, a catheter system 111 is inserted into the vicinity of the heart from a foot base through an artery. In a case of an optical coherence tomography apparatus, the vascular diagnosis apparatus 100 emits measurement light and receives the reflected light incident thereon via a probe of the catheter system 111. In this manner, the vascular diagnosis apparatus 100 acquires the tomographic image, and acquires the X-ray image (angiographic image) captured by an X-ray radiographing apparatus 200 functioning as an X-ray image acquisition unit, via a cable 103. In accordance with an exemplary embodiment, in a case of an intravascular ultrasound apparatus, the vascular diagnosis apparatus 100 outputs an ultrasound wave signal and inputs the reflected signal via the probe of the catheter system 111. In this manner, the vascular diagnosis apparatus 100 acquires the tomographic image, and acquires the X-ray image captured by the X-ray radiographing apparatus 200, via the cable 103.

Figure 2A:
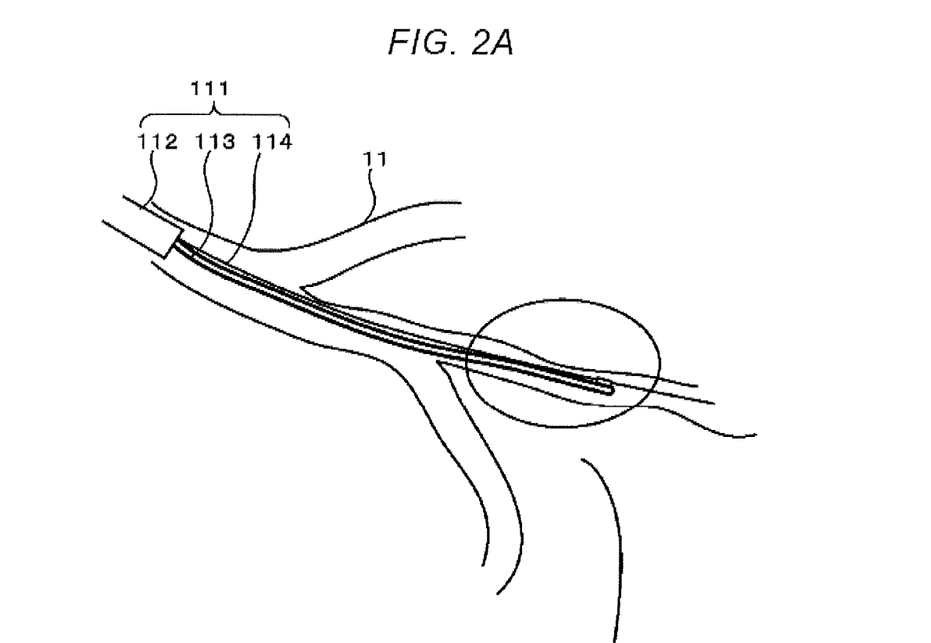
FIGS. 2A and 2B are views for describing a catheter system for acquiring a blood vessel tomographic image.
Figure 2B:
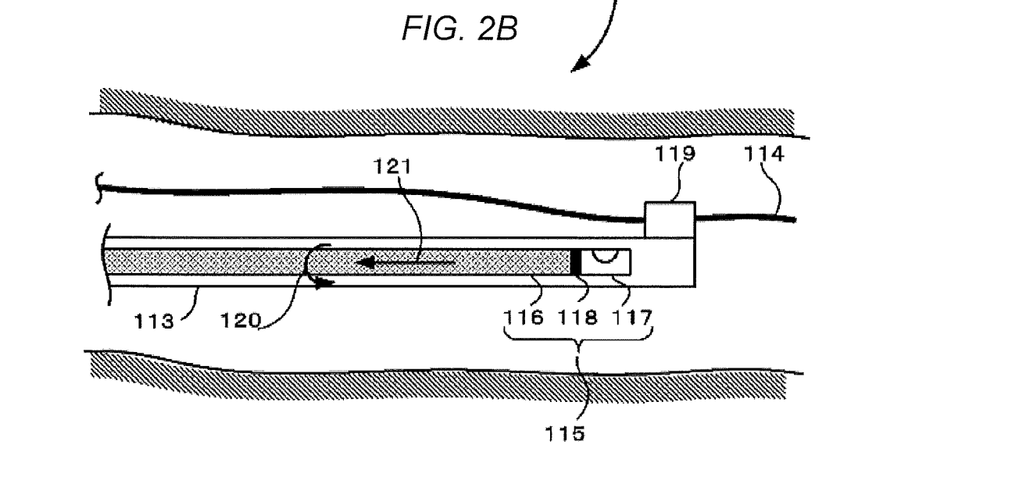

FIGS. 2A and 2B are views for describing the catheter system 111. As illustrated in FIGS. 2A and 2B, the catheter system 111 can include a guiding catheter 112, a catheter 113 internally having a probe 115 for capturing the tomographic image, and a guide wire 114. The guiding catheter 112 has a hollow for inserting the guide wire 114 and the catheter 113. For example, in a case where the tomographic image of a coronary artery is captured, a physician inserts the guiding catheter 112 into the vicinity of the coronary artery. Thereafter, the physician delivers the guide wire 114 to an imaging region through the inside of the guiding catheter 112. Then, the physician delivers the catheter 113 along the guide wire 114, and delivers an imaging core 117 of the catheter 113 to the imaging region in coronary artery. A guide wire lumen 119 is disposed in the catheter 113, and the guide wire 114 is caused to pass through the guide wire lumen 119, thereby enabling the catheter 113 to move forward along the guide wire.

The probe 115 for capturing the tomographic image can include a metal shaft 116, the imaging core 117, and a radiopaque marker 118. In a case of tomography using OCT, the imaging core 117 is connected to a distal end of an optical fiber passing through the inside of the metal shaft 116. The imaging core 117 can include an optical component which emits and receives measurement light by using a distal end portion of the optical fiber. In accordance with an exemplary embodiment, in a case of tomography using IVUS, a signal line passing through the inside of the metal shaft 116 is connected to the imaging core 117 including an ultrasound transducer for transmitting and receiving an ultrasound wave signal. While being rotatably driven (rotated in a direction of an arrow 120), the metal shaft 116 moves in an axial direction of the catheter (moves in a direction of an arrow 121) (hereinafter, referred to as a pullback). While being rotated together with the metal shaft 116, the imaging core 117 also moves in the axial direction of the catheter. The tomographic image is acquired by rotating the imaging core once. Accordingly, the tomographic image acquired while the rotating imaging core 117 moves becomes multiple blood vessel tomographic images along a blood vessel route. The radiopaque marker 118 for recognizing a position of the imaging core 117 on the X-ray image is disposed between the imaging core 117 and the metal shaft 116. The radiopaque marker 118 may be disposed on a distal side of the imaging core 117.

Referring back to FIG. 1, the tomographic image (in the present embodiment, the blood vessel tomographic image) acquired by IVUS or OCT is stored in a blood vessel tomographic image storage unit 101. A frame rate of the tomographic image captured by the vascular diagnosis apparatus 100, for example, is approximately 160 to 180 Hz. The vascular diagnosis apparatus 100 and the X-ray radiographing apparatus 200 are connected to each other by the cable 103. The X-ray image acquired by the X-ray radiographing apparatus 200 is transmitted to the vascular diagnosis apparatus 100. In the present embodiment, communication between the vascular diagnosis apparatus 100 and the X-ray radiographing apparatus is performed via a cable. However, without being limited thereto, wireless communication may be employed.

The X-ray radiographing apparatus 200 drives an X-ray source 211 so as to irradiate the patient 10 with an X-ray, and causes an X-ray sensor 212 to detect the transmitted X-ray, thereby acquiring the X-ray image (for example, the angiographic image). The acquired X-ray image is transmitted to the vascular diagnosis apparatus 100 via the cable 103, and is stored in an X-ray image storage unit 102. A frame rate of the X-ray image in the X-ray radiographing apparatus 200 is approximately 7 to 30 Hz, for example. The vascular diagnosis apparatus 100 causes the X-ray image storage unit 102 to separately store a pullback X-ray image captured before the above-described pullback starts (the blood vessel tomographic image starts to be captured) and an ongoing pullback X-ray image captured during the pullback (while the blood vessel tomographic image is captured).

An image display device 300 synchronously displays the X-ray image and the blood vessel tomographic image, and highlights a position of the radiopaque marker 118 on the X-ray image. In the image display device 300, a blood vessel model generation unit 301 generates multiple blood vessel models, based on multiple pullback X-ray images read from the X-ray image storage unit 102 by a pre-pullback X-ray image reading unit 302. A group of the generated blood vessel models is stored in a blood vessel model storage unit 303. Generation of the blood vessel models will be described in detail later.

A marker detection unit 304 detects the position of the radiopaque marker 118 from the ongoing pullback X-ray image read from the X-ray image storage unit 102 by an ongoing pullback X-ray image reading unit 305. The marker detection unit 304 according to the present embodiment fits the blood vessel model generated by the blood vessel model generation unit 301 into the ongoing pullback X-ray image, thereby estimating the position on the image of the radiopaque marker 118. The marker detection unit 304 sets a searching range of the radiopaque marker 118 to be in the vicinity of the estimated position, thereby improving detection accuracy of the radiopaque marker 118.

The blood vessel tomographic image reading unit 306 reads the blood vessel tomographic image stored in the blood vessel tomographic image storage unit 101, and provides the blood vessel tomographic image for a synchronous display unit 307. The synchronous display unit 307 performs display control on a display 308 so as to synchronously display the ongoing pullback X-ray image read by the ongoing pullback X-ray image reading unit 305 and the blood vessel tomographic image read by the blood vessel tomographic image reading unit 306. In the synchronous display, the ongoing pullback X-ray image and the blood vessel tomographic image, both of which have mutually correlated imaging timing, are displayed. In addition, in the synchronous display, the synchronous display unit 307 highlights and displays the position of the radiopaque marker 118 on the ongoing pullback X-ray image which is detected by the marker detection unit 304.

Figure 3:
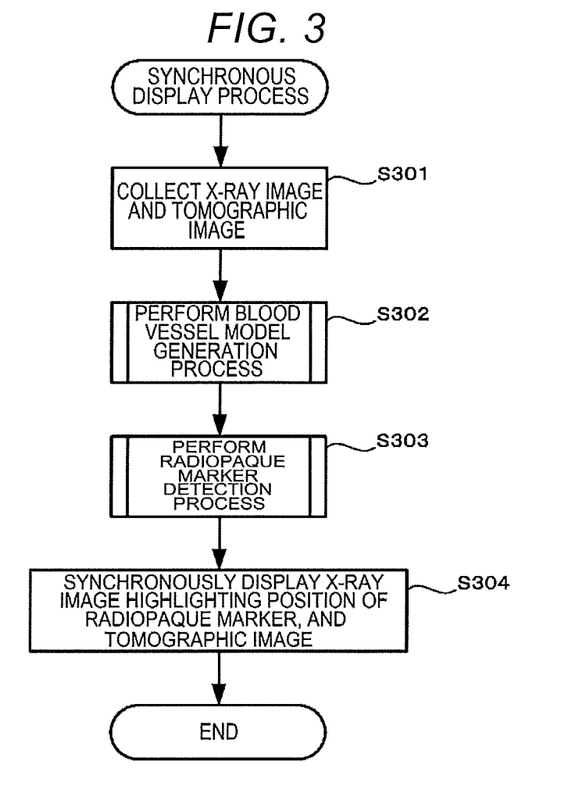
FIG. 3 is a flowchart illustrating a synchronous display process performed by the display system according to the embodiment.

An operation of the image display device 300 according to the present embodiment including the above-described configuration will be described. FIG. 3 is a flowchart illustrating a process for synchronously displaying the blood vessel tomographic image and the X-ray image (angiographic image) according to the present embodiment.

First, in Step S301, the vascular diagnosis apparatus 100 collects the blood vessel tomographic image and the X-ray image. Collection of the images in Step S301 will be described with reference to FIG. 4.

Figure 4:
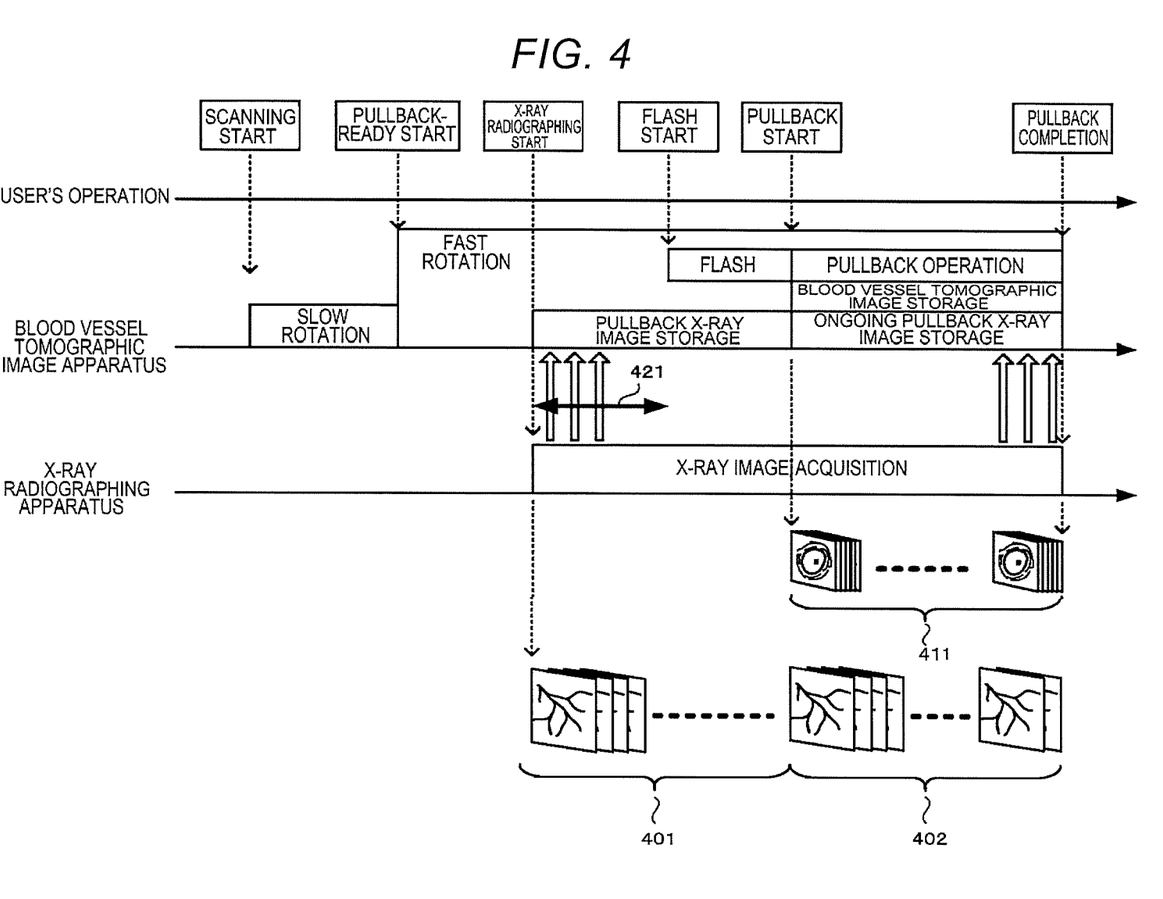
FIG. 4 is a view for describing timing to collect the blood vessel tomographic image and an X-ray image.

FIG. 4 is a view for describing timing to collect the X-ray image and the blood vessel tomographic image according to the present embodiment. If a user instructs scanning start through an operation panel (not illustrated) of the vascular diagnosis apparatus 100, the vascular diagnosis apparatus 100 starts to rotate the metal shaft 116 (and the imaging core 117) slowly inside the catheter 113. Thereafter, if the user instructs pullback-ready start through the operation panel of the vascular diagnosis apparatus 100, the vascular diagnosis apparatus 100 starts to rotate the metal shaft 116 (and the imaging core 117) fast. If the imaging core 117 is rotated fast, the imaging core 117 is brought into a state where the tomographic image can start to be captured while the pullback is performed.

After the pullback-ready start, the user instructs the X-ray radiographing apparatus 200 to start X-ray radiography through the operation panel (not illustrated) of the vascular diagnosis apparatus 100. If the X-ray radiographing apparatus 200 is instructed to start the X-ray radiography, the X-ray radiographing apparatus 200 irradiates a patient with an X-ray from the X-ray source 211, and causes the X-ray sensor 212 to capture the X-ray image. The acquired X-ray image is transmitted to the vascular diagnosis apparatus 100 via the cable 103. The vascular diagnosis apparatus 100 causes the X-ray image storage unit 102 to store the X-ray image received until the pullback start is instructed, as the pullback X-ray image. In this way, a pullback X-ray image group 401 is stored in the X-ray image storage unit 102. Only the image corresponding to one heartbeat from when the X-ray radiography starts may be stored.

A user starts a flash after instructing to start the X-ray radiography. In the flash, a contrast agent is dispensed into the blood vessel. Therefore, in a state where the contrast agent is not contained therein, the catheter immediately before performing the pullback is entirely reflected on the X-ray image group captured by the X-ray radiographing apparatus 200 during a period 421 from when the X-ray radiography starts until the flash starts. According to the present embodiment, a blood vessel model (to be described later) is prepared using an image group captured during the period 421 in the pullback X-ray image group 401.

If the user instructs pullback start, the vascular diagnosis apparatus 100 starts the pullback of the imaging core 117, and starts to generate the blood vessel tomographic image. A blood vessel tomographic image group 411 acquired during the pullback operation is stored in the blood vessel tomographic image storage unit 101. In addition, the X-ray image group acquired by the X-ray radiographing apparatus 200 during the pullback operation is stored in the X-ray image storage unit 102 as an ongoing pullback X-ray image group 402. In a state where the contrast agent is contained therein, an interest region of the blood vessel in which the pullback is performed is reflected on the ongoing pullback X-ray image, and the radiopaque marker 118 moving in accordance with the pullback of the imaging core 117 is reflected on the ongoing pullback X-ray image.

If the blood vessel tomographic image (the blood vessel tomographic image group 411) and the X-ray image (the pullback X-ray image group 401 and the ongoing pullback X-ray image group 402) are completely collected as described above, the process proceeds to Step S302. In Steps S302 and S303, a radiopaque marker detection process is performed by the image display device 300 according to the present embodiment. First, in Step S302, the blood vessel model generation unit 301 of the image display device 300 generates the blood vessel model by using an image of the pullback X-ray image group 401 stored in the X-ray image storage unit 102. Hereinafter, a generation process of the blood vessel model which is performed by the blood vessel model generation unit 301 will be described in more detail with reference to a flowchart in FIG. 5.

Figure 5:
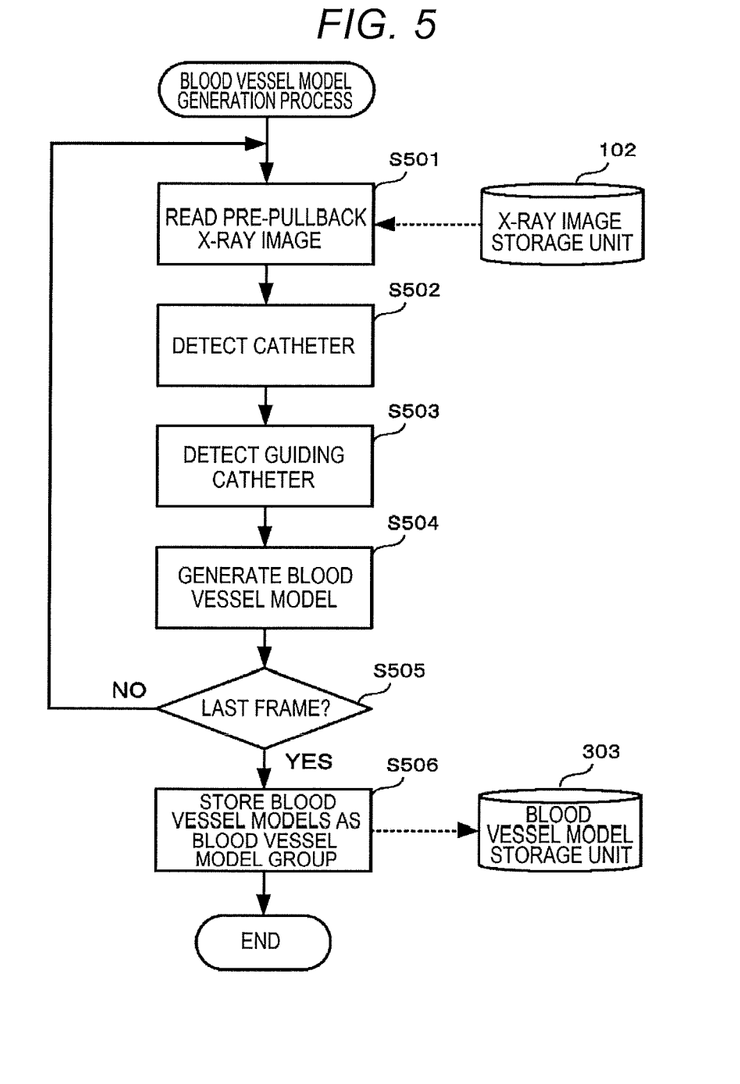
FIG. 5 is a flowchart for describing a blood vessel model generation process.

First, in Step S501, the pre-pullback X-ray image reading unit 302 reads the pullback X-ray image corresponding to a predetermined period within the period 421 from the pullback X-ray image group 401 stored in the X-ray image storage unit 102. According to the present embodiment, in order to align the blood vessel model corresponding to at least one heartbeat with the above described predetermined period, the predetermined period employs a period (for example, one second) set so as to include a period corresponding to at least one heartbeat, within the period 421 from when the X-ray radiography starts until the flash starts.

As long as the catheter is in an indwelling state and the predetermined period is set to a period before the pullback and the flash start, the predetermined period is set as follows, for example.

The predetermined period is specified, based on timing when a user's instruction to start the X-ray radiography is detected. For example, the predetermined period is set to one second until one second later from when the instruction to start the X-ray radiography is detected, or one second until one second to two seconds later from when the instruction to start the X-ray radiography is detected.

Based on the timing when the flash start is detected, the earlier period (for example, three seconds to two seconds earlier than the timing to detect the flash start) is used as the predetermined period. The flash start can be detected by detecting a change in the X-ray image (for example, by detecting an increase in a dark portion region).

In the above-described example, in accordance with a user's instruction to start the X-ray radiography, the X-ray image starts to be stored, and the pullback X-ray image corresponding to the period 421 is read in order to generate the blood vessel model. However, a configuration is not limited thereto. For example, the X-ray images may be collected in advance from before the tomographic image starts to be acquired (pullback operation) until after the multiple tomographic images are acquired (after the pullback operation is completed). In this manner, based on the collected X-ray images, the timing to start the X-ray radiography may be determined, and the X-ray images may be acquired during the predetermined period from the determined timing. Automatic determination of the timing to start the X-ray radiography, based on the X-ray image, is performed by detecting whether or not there is a specific note such as "under imaging" included in the X-ray image or detecting a darkened X-ray image when the imaging starts.

Figure 6A:
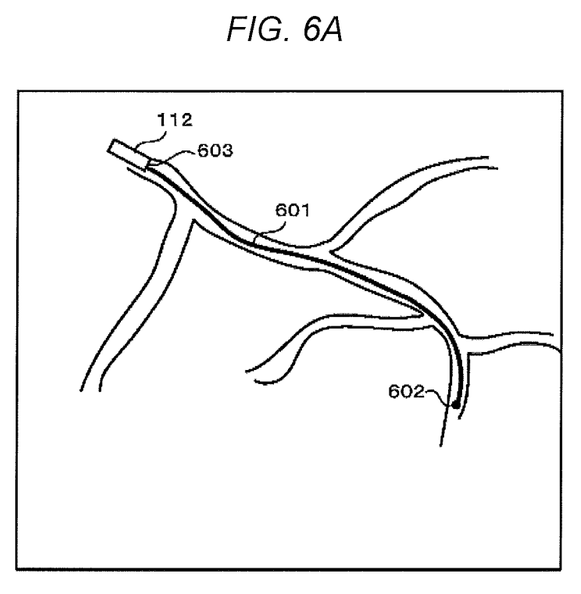
FIGS. 6A and 6B are views for describing the blood vessel model generation process according to the embodiment.

Next, in Step S502, the blood vessel model generation unit 301 detects a line (shape of a catheter arranged inside the blood vessel, and corresponding to a trajectory in which the radiopaque marker 118 moves) extending along a catheter 113 (probe 115) from the read pullback X-ray image. The probe 115 inside the catheter 113 used for the vascular diagnosis apparatus 100 has the metal shaft 116 for rotating the imaging core 117. The metal shaft 116 has a lower X-ray transmittance, compared to that of other living body tissues, and appears as a black linear object 601 on the X-ray image as illustrated in FIG. 6A. In addition, as described above with reference to FIG. 2B, the radiopaque marker 118 is arranged in the distal end of the probe 115 of the catheter 113 so that the position of the distal end can be easily recognized on the X-ray image. The radiopaque marker 118 appears as a black dot 602 on the X-ray image.

Based on the above-described characteristics, the catheter distal end (black dot 602) can be automatically recognized using a general image processing technique, for example, such as pattern matching and gray searching. In addition, the catheter 113 entirely appears as a black line from the above-described catheter distal end. Accordingly, the catheter 113 can be automatically recognized by using a general route searching technique after an adaptive binarization filter is adapted thereto. The pullback X-ray image corresponding to the predetermined period within the period 421 does not contain the contrast agent. Accordingly, the black linear object 601 and the black dot 602 are relatively clear, and thus, these can be accurately extracted.

Next, in Step S503, the blood vessel model generation unit 301 detects a distal portion (hereinafter, referred to as a GC inlet) of the guiding catheter 112 on the pullback X-ray image. As described above, according to a technique using the catheter, in order to insert a required device into the blood vessel, the guiding catheter 112, which is a hollow tube is inserted into the blood vessel. An observation target site (acquisition range of the blood vessel tomographic image acquired by performing the pullback) of the vascular diagnosis apparatus 100 is present from the probe distal end detected in Step S502 to the GC inlet. Accordingly, in order to determine the observation target site, a position of the GC inlet is obtained on the pullback X-ray image. In a state where the contrast agent is not contained therein, a shape of the GC inlet portion has a cylindrical shape even if any type of guiding catheters is employed. Accordingly, the GC inlet can also be automatically and accurately detected using a general pattern matching method.

A user may specify the GC inlet portion by directly designating the GC inlet portion on the pullback X-ray image. Alternatively, the GC inlet portion may be detected from another X-ray image group corresponding to one heartbeat by using information around the GC inlet portion designated by the user on the specified pullback X-ray image.

A frame rate of the image captured by the X-ray radiographing apparatus 200 is approximately 7 to 30 Hz, for example. Accordingly, the X-ray images corresponding to one second are approximately 7 to 30 sheets, for example. Therefore, the catheter may be detected by the user designating the catheter distal end and the entire body. In addition, a position of the catheter distal end may be automatically detected on the X-ray image group corresponding to one heartbeat by the user designating the catheter distal end at a single frame and using a feature amount of the image around the designated catheter distal end.

Figure 6B:
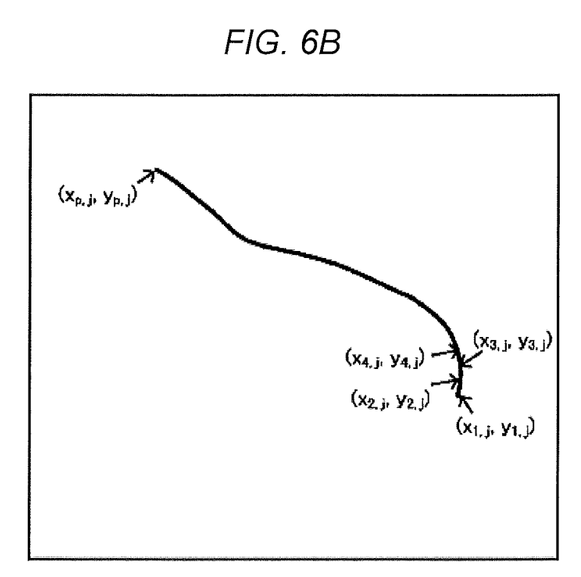

In Step S504, the blood vessel model generation unit 301 defines coordinates of a trajectory from the distal end of the catheter 113 detected in Steps S502 and S503 to the GC inlet, as the blood vessel model. For example, the blood vessel model generation unit 301 extracts the black linear object 601 from the position of the GC inlet 603 to the position of the black dot 602 which are illustrated in FIG. 6A, as a line extending along the catheter 113 within the acquisition range of the blood vessel tomographic image. Then, as illustrated in FIG. 6B, the blood vessel model generation unit 301 equally divides the trajectory (extracted line) from the distal end of the catheter 113 to the GC inlet into p-1 pieces. The coordinate of the distal end is set to $(x_{1,j}, y_{1,j})$, and the coordinate of the GC inlet is set to $(x_{p,j}, y_{p,j})$. After x and y coordinates of each position is obtained, the coordinates are defined as the blood vessel model. The blood vessel model generated as described above is stored in the blood vessel model storage unit 303. Here, j represents the number of the blood vessel models. If the j-number of the pullback X-ray images is acquired from the predetermined period, j is provided with a value of 1 to J.

In Step S505, it is determined whether or not the last X-ray image (J-th X-ray image, hereinafter, referred to as the last frame) of the pullback X-ray images within the above-described predetermined period is processed. If the last frame is not processed, the process returns to Step S501, and the above-described process is performed on the subsequent pullback X-ray image within the predetermined period.

As described above, if the blood vessel model is generated from all of the pullback X-ray images within the predetermined period, the process proceeds from Step S505 to Step S506. In Step S506, the blood vessel model generation unit 301 causes the blood vessel model storage unit 303 to store a blood vessel model group (in the present embodiment, the J-number of blood vessel models) generated in Steps S501 to S505. The blood vessel model group including the blood vessel model corresponding to one heartbeat is generated and stored as described above. The blood vessel model group indicates a position (position of the blood vessel) of the catheter 113 which corresponds to the heartbeat. In Step S504 described above, the coordinates are maintained as the blood vessel model, but a configuration is not limited thereto. For example, image data (for example, an image as illustrated in FIG. 6B in which the trajectory of the catheter 113 from the detected catheter distal end to the GC inlet is white (or black) and others are black (or white) may be maintained as the blood vessel model group.

As described above, if the blood model is generated by the blood vessel model generation unit 301, the process proceeds to Step S303 in FIG. 3. In Step S303, the marker detection unit 304 uses the blood vessel model group generated in Step S302 so as to detect the position of the radiopaque marker 118 for each X-ray image of the ongoing pullback X-ray image group 402. Hereinafter, a marker detection process performed by the marker detection unit 304 will be described with reference to a flowchart in FIG. 7.

Figure 7:
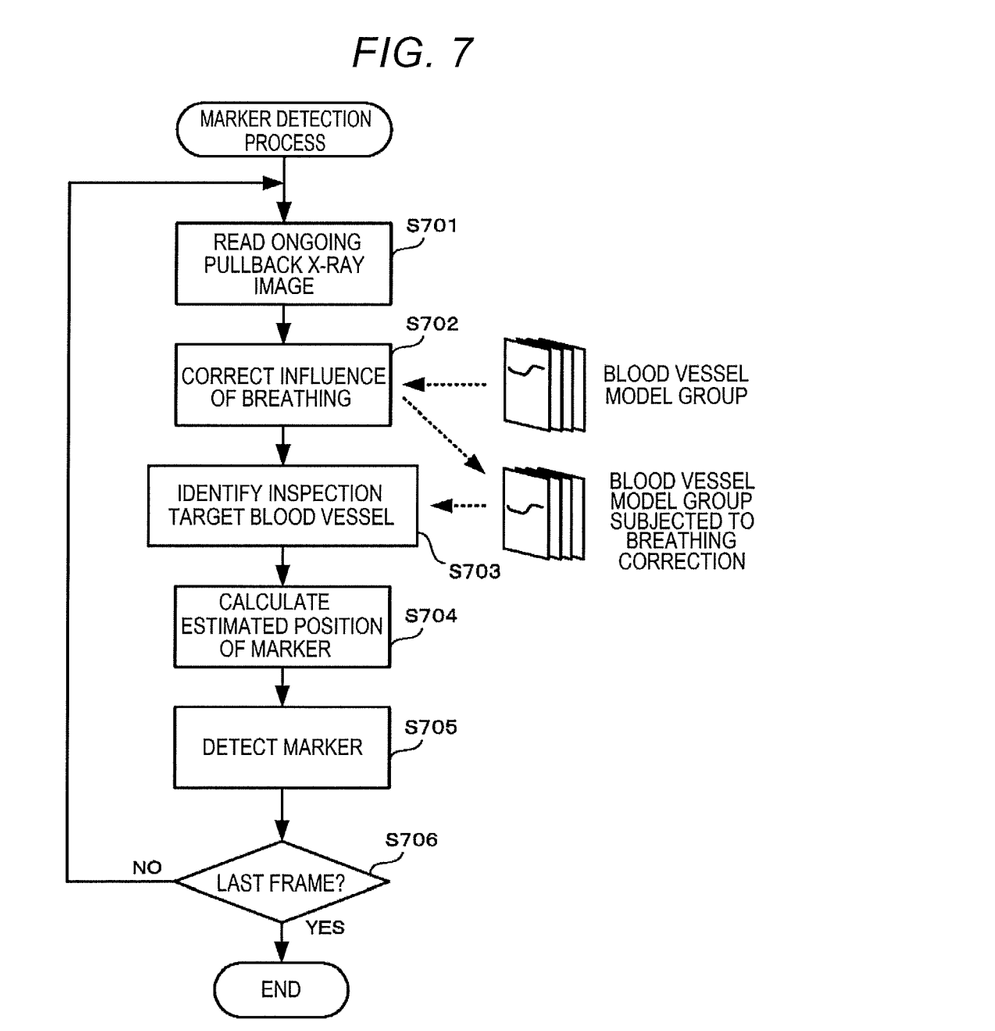
FIG. 7 is a flowchart for describing a marker detection process.

In Step S701, the ongoing pullback X-ray image reading unit 305 reads the ongoing pullback X-ray image from the X-ray image storage unit 102. Next, in Step S702, the marker detection unit 304 corrects deviation between a breathing condition of a subject and a breathing condition during the acquisition of each blood vessel model on the X-ray image read in Step S701, that is, influence of the breathing (hereinafter, referred to as breathing correction).

The breathing represents oscillating movement in conjunction with diaphragmatic movement. While the catheter is manually operated, natural breathing is managed for a patient. Accordingly, in general, the oscillating movement occurs approximately 0.3 times per frame. A change caused by the heartbeat results in parallel movement, rotation, or deformation of the blood vessel. In contrast, a change caused by the breathing mainly results in parallel movement of the blood vessel. Therefore, in the breathing correction, movement (parallel movement) is corrected in vertical and lateral directions of the entire blood vessel on the X-ray image. For example, in the breathing correction according to the present embodiment, the position of the GC inlet portion on the ongoing pullback X-ray image is detected by using a pattern matching method, and the blood vessel model is moved parallel so that the GC inlet portion of the blood vessel model is coincident with the detected position of the GC inlet portion. In some cases, it can be difficult to detect the GC inlet from the entire X-ray image. Accordingly, a user may designate the GC inlet for only the first frame, and may trace the position of the GC inlet of the preceding frame for the subsequent frames.

As another method, a movement amount generated by breathing may be obtained by detecting the diaphragmatic movement which is present on the X-ray image. The diaphragm is normally confirmed as a low bright and uniform image on the X-ray image. Brightness of the entire X-ray image can be classified into three regions such as (1) the blood vessel image which is the lowest bright region and which has the contrast agent contained therein, (2) a diaphragm region which is the subsequently lowest bright region (region having an intermediate brightness value), and (3) a region other than (1) and (2). Accordingly, the vertical and lateral movement amount generated by the breathing can be detected by tracing the center of the image having the brightness classified into the above-described (2), for example, when the brightness is classified into three by using a clustering method. If the position of the GC inlet is designated by a user for the leading frame, the position of the GC inlet in the subsequent frames can be determined by the movement amount obtained based on the displacement of the above-described diaphragm.

As a still another method, instead of detecting the movement of the above-described GC inlet, movement of a radiopaque marker (not illustrated) disposed on the distal side of the catheter 113 (hereinafter, referred to as a distal marker) may be detected. In general, the distal marker has a larger size than the radiopaque marker 118 arranged in the vicinity of the imaging core 117, and can be detected as a clearer black dot.

The displacement caused by the breathing mainly occurs in the vertical direction. Accordingly, correction may be performed in the vertical direction only.

The breathing correction of the blood vessel model will be described in more detail. In a case where a coordinate group of the j-th frame of the blood vessel model is set to $(X_j, Y_j)$, the coordinate group is expressed by Expression 1 below.

$$(X_j, Y_j) = \{(x_{1,j}, y_{1,j}) \ldots (x_{p,j}, y_{p,j})\} \quad \text{Expression 1}$$

Here, the p-number of coordinates of the blood vessel model is present, and the coordinates are stored so that an index increases from a distal side (radiopaque marker side) to a proximal side (GC inlet side). In addition, x represents a coordinate in the lateral direction on the X-ray image, and y represents a coordinate in the vertical direction on the X-ray image.

If the coordinate of the GC inlet portion on the ongoing pullback X-ray image which is a process target is set to $(x_{GC}, y_{GC})$ and the coordinate of the GC inlet portion of the blood vessel model is set to $(x_{p,j}, y_{p,j})$, a coordinate group $(X'_j, Y'_j)$ of the blood vessel model after the breathing correction is expressed by Expression 2 below.

$$(X'_j, Y'_j) = (X_j, Y_j) - ((x_{p,j}, y_{p,j}) - (x_{GC}, y_{GC})) \quad \text{Expression 2}$$

In Step S702, the above-described breathing correction is performed on all of the blood vessel models stored in the blood vessel model storage unit 303, thereby generating the blood vessel model group subjected to the breathing correction.

Next, in Step S703, the marker detection unit 304 selects the blood vessel model corresponding to the inspection target blood vessel by using the blood vessel model subjected to the breathing correction. The blood vessel model generated by the blood vessel model generation unit 301 represents information of the trajectory from the GC inlet portion to the catheter distal portion in each heartbeat. The marker detection unit 304 detects the blood vessel model subjected to the breathing correction (that is, the blood vessel model corresponding to the ongoing pullback X-ray image in which a heartbeat cycle is a process target) which is adapted to the ongoing pullback X-ray image under processing. Hereinafter, the process will be described.

First, an adaptive binarization filter is used so as to binarize the ongoing pullback X-ray image. A brightness value corresponding to the coordinate of the blood vessel model in which the obtained binarized image is subjected to the breathing correction is used so as to calculate a correlation value $R_j$ for the j-th blood vessel model by using Expression 3 below, for example.

$$R_j = \sum_{i=1}^{m} k_i \times I(x'_{i,j}, y'_{i,j}) \quad \text{Expression 3}$$

$$k_{i+1} = \begin{cases} k_i + 1 & \text{if } I(x'_{i,j}, y'_{i,j}) > 0 \\ 0 & \text{otherwise} \end{cases}$$

Here, $I(x'_{i,j}, y'_{i,j})$ represents a pixel value in a coordinate $(x'_{i,j}, y'_{i,j})$ of the ongoing pullback X-ray image subjected to binarization. According to the present embodiment, the contrast agent is dispensed into the blood vessel. Through the above-described binarization, the blood vessel image of the blood vessel containing the contrast agent appears as black, and other regions appear as white. Accordingly, if the coordinate $(x'_{i,j}, y_{i,j})$ is located on the blood vessel image containing the contrast agent, a value of $I(x'_{i,j}, y_{i,j})$ represents 1. If the coordinate $(x'_{i,j}, y_{i,j})$ is located on other regions, the value of $I(x'_{i,j}, y_{i,j})$ represents 0. In addition, k represents the weight for considering continuity of the blood vessel. In a case where the position (coordinate $(x'_{i,j}, y_{i,j})$) of the blood vessel model is continuously present on the blood vessel image, a weight value increases. As a matter of course, a weighting may not be used. In a case where the weighting is not used, it always shows $k_i=1$.

Figure 8A:
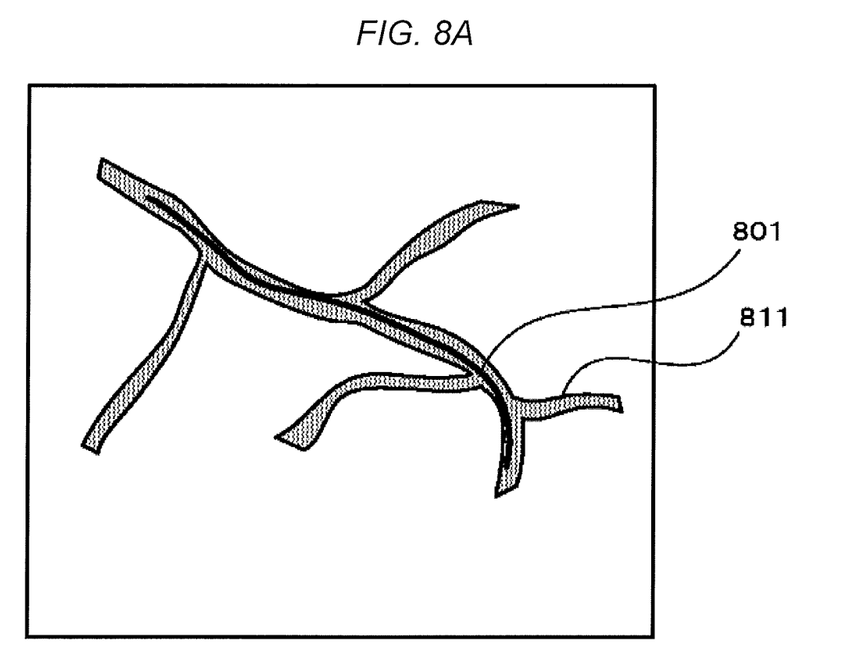
FIGS. 8A and 8B are views for describing selection of a blood vessel model in marker detection according to the embodiment.
Figure 8B:
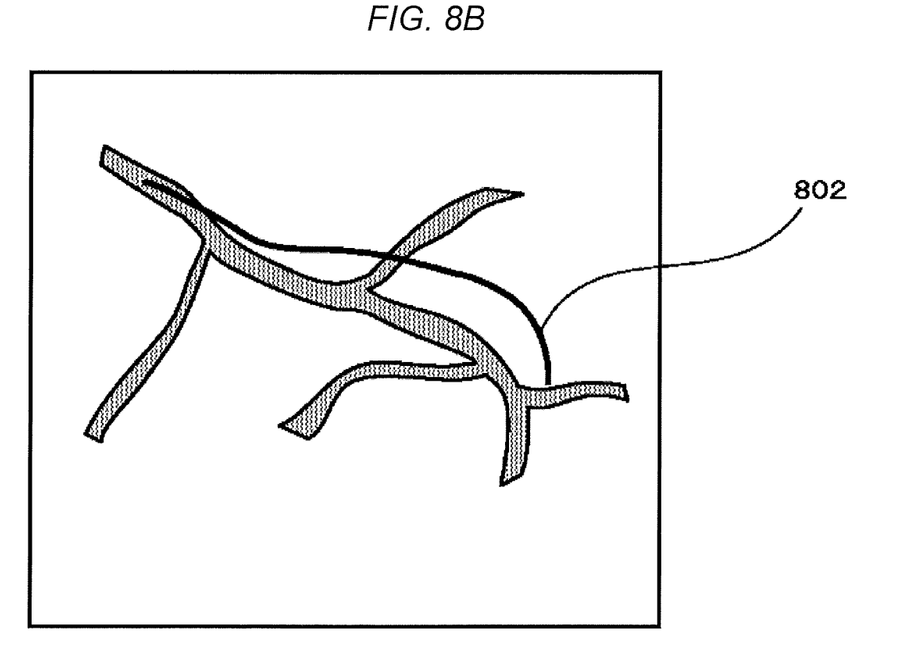

According to the above-described calculation, a correlation value R to be calculated increases in a blood vessel model 801 which has many portion overlapping a blood vessel image 811 as illustrated in FIG. 8A. The correlation value R to be calculated decreases in a blood vessel model 802 deviated from the blood vessel image 811 as illustrated in FIG. 8B. According to the present embodiment, the j-number of blood vessel models is generated. Accordingly, a correlation value is calculated for each blood vessel model of j=1 to J, thereby employing the blood vessel model indicating the greatest correlation ($R_j$ becomes the maximum) as the blood vessel model for the ongoing pullback X-ray image which is a process target.

Next, in Step S704, the marker detection unit 304 uses the blood vessel model selected in Step S703 so as to estimate the position of the radiopaque marker 118 on the ongoing pullback X-ray image. The catheter 113 of the vascular diagnosis apparatus 100 is supposed to be present on the blood vessel model (trajectory of the catheter) selected during the above-described process. Furthermore, it can be assumed that the probe (the imaging core 117 and the radiopaque marker 118) moves on the blood vessel model from the distal position of the catheter toward the GC inlet at equal speed.

The blood vessel model selected in Step S703 represents the trajectory from the probe distal end to the GC inlet before the pullback. If it is considered that the ongoing pullback X-ray image is collected in synchronization with the pullback operation performed by the vascular diagnosis apparatus 100, a distance obtained in such a way that the selected blood vessel model is equally divided by the number of frames (number of the blood vessel tomographic image groups 411) from when the pullback starts until the GC inlet is detected on the blood vessel tomographic image represents a unit distance Δl in which the radiopaque marker moves on the X-ray image. The GC inlet on the blood vessel tomographic image is drawn as a substantially circular shape whose entire circumference is very bright, and is very characteristic, compared to a normal blood vessel image. Therefore, the GC inlet can be easily detected from the blood vessel tomographic image. If the number of the blood vessel tomographic image groups 411 from when the pullback starts until the GC inlet is displayed is set to N and the total length of the selected blood vessel model is set to L, the unit distance Δl is expressed as follows.

$$\Delta l = L/(N-1) \qquad \text{Expression 4}$$

However, whereas the X-ray images are normally collected at a sampling rate of 7, 15, and 30 Hz, the blood vessel tomographic images are collected at 30 Hz or greater (for example, 160 and 180 Hz). Accordingly, with regard to a single movement distance of the radiopaque marker on the X-ray image which can be actually acquired, it is necessary to consider a difference in the frame rates. Therefore, an estimated position of the radiopaque marker 118 on the m-th ongoing pullback X-ray image is present at a position away from the distal portion (pullback start position) on the selected blood vessel mode as far a distance $L_m$ expressed by Expression 5 below.

$$L_m = \frac{L f_o}{(N-1) f_a} m \qquad \text{Expression 5}$$

Here, $f_0$ represents a sampling rate (Hz) of the blood vessel tomographic image, and $f_a$ represents a sampling rate (Hz) of the X-ray image.

A length li from a distal portion $(x_{1,j}, y_{1,j})$ corresponding to the i-th index coordinate of the selected blood vessel model is expressed by Expression 6 below.

$$l_i = \sum_{w=2}^{i} \sqrt{(x'_{w-1,j} - x'_{w,j})^2 + (y'_{w-1,j} - y'_{w,j})^2} \qquad \text{Expression 6}$$

$$l_i \le L_m < l_{i+1} \qquad \text{Expression 7}$$

Therefore, a coordinate position corresponding to the i-th index (or i+1-th index) of the blood vessel model which satisfies Expression 7 above is set to the estimated position of the radiopaque marker 118. Alternatively, a result obtained through linear interpolation using the coordinate position corresponding to the i-th index and the coordinate position corresponding to the i+1-th index may be set to the estimated position. In this case, if the coordinate corresponding to the i-th index is set to $(X_i, Y_{i+1})$ and the coordinate corresponding to the i+1-th index is set to $(X_{i+1}, Y_{i+1})$, Estimated Position=$(k*X_i+(1-k)*X_{i+1}, k*Y_i+(1-k)*Y_i)$ and $k=(l_{i+1}-L_m)/(l_{i+1}-l_i)$ are satisfied. Accuracy of the estimated position may be improved in such a way that the estimated position is obtained by feeding back the position of the radiopaque marker 118 in the preceding frame to the estimated position.

As described above, if the position of the radiopaque marker 118 on the ongoing pullback X-ray image is estimated based on the blood vessel model, the process proceeds to Step S705. In Step S705, the marker detection unit 304 searches for the radiopaque marker 118 in the vicinity of the position estimated in Step S704, and determines the position of the radiopaque marker.

As described above, the radiopaque marker 118 appears as a black dot on the X-ray image. Accordingly, the marker detection unit 304 performs a process for emphasizing the black dot within a specified range (for example, the vicinity of the estimated position) based on the estimated position of the radiopaque marker 118 estimated in Step S704. As this process, a filter for emphasizing the black dot (for example, a convolution filter or frequency analysis (wavelet or FFT)) may be used.

As a result of the filter process, multiple candidate dots are generally found out. Accordingly, the marker detection unit 304 obtains the correlation with the radiopaque marker 118, thereby selecting a highly correlated candidate dot as the radiopaque marker 118. For example, the following correlation value can be used.

Distance Correlation Value

Square Value of Distance between Estimated Position and Detected Position

Alternately, Square Value of Distance between Blood Vessel Model and Detected Position Shape Correlation Value As described above, the radiopaque metal shaft 116 is present on the rear side of the radiopaque marker. In addition, with regard to a structure of the catheter 113, the inside of the catheter 113 on the distal side from the radiopaque marker 118 is filled with air or a radiolucent component such as saline. Accordingly, with regard to a shape, a brightness value decreases in the proximal portion direction of the blood vessel model from the detected position of the radiopaque marker 118, and the brightness value increases in the end portion direction. A one-dimensional filter simulating this shape is adapted in the blood vessel model direction from the detected position of the black dot, thereby determining the correlation.

Next, in Step S706, the marker detection unit 304 determines whether or not the above-described process is completely performed on all of the ongoing pullback X-ray images. If there is the ongoing pullback X-ray image which is not processed, the process returns to Step S701. The processes in Steps S701 to S705 are performed on the subsequent ongoing pullback X-ray image. If the marker is detected for all of the ongoing pullback X-ray images in this way, the marker detection process is completed.

Referring back to FIG. 3, in Step S304, the synchronous display unit 307 causes the display 308 to synchronously display the blood vessel tomographic image and the ongoing pullback X-ray image. If the N-number of the blood vessel tomographic images and the M-number of the ongoing pullback X-ray images are obtained during the pullback operation, the synchronous display unit 307 performs control so as to concurrently display the n-th blood vessel tomographic image and the $m = f_a/f_o * n$-th ongoing pullback X-ray image. Here, $f_o$ represents a sampling rate (Hz) of the blood vessel tomographic image, and $f_a$ represents a sampling rate (Hz) of the X-ray image. Through the marker detection process, the position of the radiopaque marker 118 is detected for each of the M-number of the ongoing pullback X-ray images. Accordingly, the synchronous display unit 307 performs highlighting for emphasizing the position of the radiopaque marker 118 on the ongoing pullback X-ray image which is under display. For example, a method of emphasizing the position of the radiopaque marker 118 can include displaying a graphic having predetermined brightness (or color) at the position detected by the marker detection unit 304, displaying the graphic in a flashing manner, or displaying an arrow graphic indicating the detected position.

Figure 9:
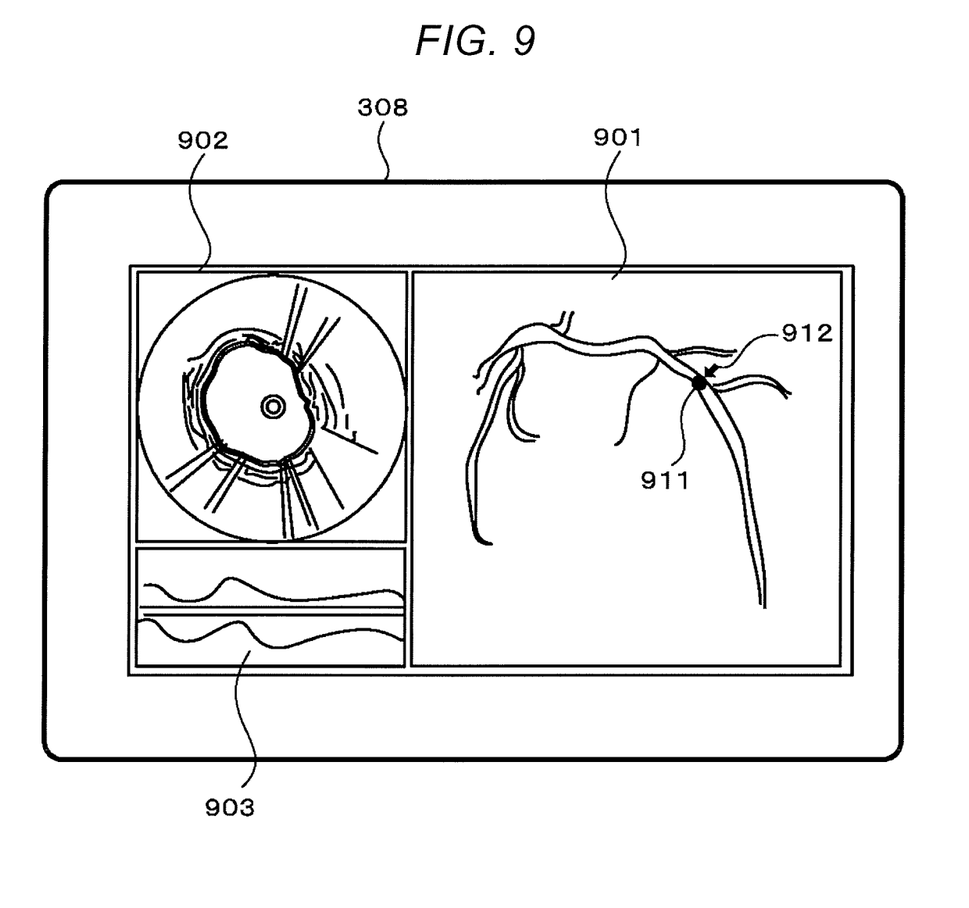
FIG. 9 is a view illustrating an example of synchronous display according to the embodiment.

FIG. 9 is a view illustrating an example of synchronous display according to the embodiment. The synchronous display unit 307 performs display control of the display 308. As illustrated in FIG. 9, the synchronous display unit 307 synchronously displays an X-ray image 901 (angiographic image) and a blood vessel tomographic image 902. In the synchronous display, the X-ray image 901 captured at the same timing as the acquisition timing of the blood vessel tomographic image 902 under display is displayed. In addition, as a display example of specifying a radiopaque marker position, FIG. 9 illustrates a state where an emphasizing mark 911 is superimposed on the radiopaque marker position and a state where an arrow graphic 912 indicates the radiopaque marker position. A shape or a color of the emphasizing mark 911 or the arrow graphic 912 is not limited to the illustrated example, and may be displayed in a flashing manner. In addition, a user's operation may switch the display of the emphasizing mark 911 or the arrow graphic 912 to be turned on or off.

As described above, according to the image display device 300 in the above-described embodiment, it is possible to very reliably detect the position of the radiopaque marker 118 on the X-ray image (angiographic image). In addition, the blood vessel tomographic image and the X-ray image (ongoing pullback X-ray image) are synchronously displayed on the display 308, thereby specifying the position of the radiopaque marker 118 on the X-ray image. Therefore, a user can easily and immediately recognize the position of the radiopaque marker 118 on the X-ray image (angiographic image) when the user captures the blood vessel tomographic image under display.

In the above-described embodiment, an example has been described in which the image display device is realized by an information processing device (for example, a general-purpose PC) independent of the vascular diagnosis apparatus 100 or the X-ray radiographing apparatus 200. However, the embodiment is not limited thereto. For example, a function of the image display device 300 may be incorporated in the vascular diagnosis apparatus 100 or the X-ray radiographing apparatus 200. In addition, in the above-described embodiment, the vascular diagnosis apparatus 100 causes the X-ray image storage unit 102 to store the X-ray image supplied from the X-ray radiographing apparatus 200. However, the X-ray radiographing apparatus 200 may store the X-ray image. In this case, the X-ray radiographing apparatus 200 receives a signal indicating an operation to start the pullback or completion of the pullback from the vascular diagnosis apparatus 100 via the cable 103. In this manner, the X-ray radiographing apparatus 200 can separately store the pullback X-ray image group 401 and the ongoing pullback X-ray image group 402.

A configuration may be adopted in which the image display device 300 can change the selection result of the blood vessel model in Step S703 in accordance with a user's operation. For example, a configuration may be adopted in which a user can select a desired blood vessel model by providing the display 308 with the J-number of breathing corrected images of the blood vessel model. The image display device 300 displays the blood vessel model selected by the user by superimposing the blood vessel model on the ongoing pullback X-ray image, thereby allowing the user to observe the superimposed display and to determine whether or not the blood vessel model is suitable. Then, in accordance with a predetermined determination operation input from the user, the blood vessel model currently selected by the user is determined as the blood vessel model corresponding to the ongoing pullback X-ray image.

In addition, a configuration may be adopted in which the position of the radiopaque marker detected in Step S705 can be corrected in accordance with the user's operation. For example, the emphasizing display on the ongoing pullback X-ray image displayed during the synchronous display is enabled to move in accordance with the user's operation such as a mouse operation. In a case where there is the user's operation to move the emphasizing display, the position of the radiopaque marker is corrected to a position of the emphasizing display after being moved.

In the synchronous display, a configuration may be adopted in which the user can set whether or not to perform a process for specifying the position of the radiopaque marker. In addition, the respective functional units provided for the image display device 300 may be realized by causing a computer (or processor) to execute a predetermined program. Alternatively, the functional units may be partially or entirely realized by hardware.

The detailed description above describes a method for detecting a position of a catheter for generating a tomographic image of a living body tissue. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An image display device that displays multiple tomographic images acquired while moving a probe in an axial direction of a catheter and multiple X-ray images captured during the movement of the probe, comprising:
   a processor configured to:
      extract a line extending along the probe from the X-ray image captured during a pre-pullback period before the probe starts to move; and
      detect a position of a radiopaque marker disposed in the probe on each of the multiple X-ray images captured during the movement of the probe following the pre-pullback period, by using the line extracted; and
   a display for synchronously displaying the multiple X-ray images and the multiple tomographic images so as to specify the position of the detected radiopaque marker on the X-ray image.

2. The image display device according to claim 1, wherein the processor is configured:
   estimate a position of the radiopaque marker on the X-ray image captured during the movement, based on the line extracted; and
   search for an image of the radiopaque marker in a vicinity of the position estimated, on the X-ray image captured during the movement.

3. The image display device according to claim 2, wherein the processor is configured:
   select a line which most closely matches a blood vessel image on the X-ray image captured during the movement, from multiple lines extracted from the multiple X-ray images captured during the pre-pullback period; and
   estimate the position of the radiopaque marker, based on the line selected.

4. The image display device according to claim 3, wherein the processor is configured:
   change a selection result of the line selected, in accordance with a user's operation.

5. The image display device according to claim 2, wherein the processor is configured:
   extract a line corresponding to a portion of the probe which is present from the position of the radiopaque marker to an end portion of a guiding catheter.

6. The image display device according to claim 5, wherein the processor is configured:
   move the line extracted line corresponding to the portion of the probe which is present from the position of the radiopaque maker to the end portion of the guiding catheter so that a position of the end portion of the guiding catheter on the X-ray image captured during the movement of the probe is coincident with a position of the line which corresponds to the end portion of the guiding catheter the line moved.

7. The image display device according to claim 1, wherein the pre-pullback period is set to include a period corresponding to at least one heartbeat, during a period from when X-ray radiography starts until a flash starts.

8. The image display device according to claim 1, wherein the processor is configured:
   collect the X-ray images captured from before the multiple tomographic images start to be acquired until after the multiple tomographic images are acquired; and
   determine timing to start acquiring X-ray images, based on the X-ray images collected, and acquire the X-ray images during the pre-pullback period, from the determined timing.

9. The image display device according to claim 1, wherein the processor is configured:
   correct the position of the radiopaque marker detected, in accordance with a user's operation.

10. The image display device according to claim 1, wherein the processor is configured:
   set whether or not to perform a process for specifying the position of the radiopaque marker.

11. An optical coherence tomography apparatus comprising:
   tomographic image acquisition unit for acquiring a tomographic image by emitting measurement light and receiving the reflected light incident thereon via the probe;
   X-ray image acquisition unit for acquiring an X-ray image captured by an X-ray radiographing apparatus; and
   the image display device according to claim 1.

12. An intravascular ultrasound apparatus comprising:
   tomographic image acquisition unit for acquiring a tomographic image by outputting an ultrasound wave signal and inputting the reflected signal via the probe;
   X-ray image acquisition unit for acquiring an X-ray image captured by an X-ray radiographing apparatus; and
   the image display device according to claim 1.

13. A control method of an image display device that displays multiple tomographic images acquired while moving a probe in an axial direction of a catheter and multiple X-ray images captured during the movement of the probe, the control method comprising:
   extracting a line extending along the probe from an X-ray image captured during a pre-pullback period before the probe starts to move;
   detecting a position of a radiopaque marker disposed in the probe on each of the multiple X-ray images captured during the movement of the probe following the pre-pullback period, by using the line extracted; and
   synchronously displaying the multiple X-ray images and the multiple tomographic images to specify the position of the detected radiopaque marker on the X-ray image.

14. The control method according to claim 13, comprising:
   estimating a position of the radiopaque marker on the X-ray image captured during the movement, based on the line extracted; and
   searching for an image of the radiopaque marker in a vicinity of the position estimated, on the X-ray image captured during the movement.

15. The control method according to claim 14, comprising:
   selecting the line which most closely matches a blood vessel image on the X-ray image captured during the movement, from multiple lines extracted from the multiple X-ray images captured during the pre-pullback period; and estimating the position of the radiopaque marker, based on the line selected.

16. The control method according to claim 15, comprising:

changing a selection result of the line selected, in accordance with a user's operation.

17. The control method according to claim 13, comprising:

setting the pre-pullback period so as to include a period corresponding to at least one heartbeat, during a period from when X-ray radiography starts until a flash starts.

18. A non-transitory computer readable storage medium that causes a processor to execute each process for the control method of the image display device according to claim 13.

19. A radiopaque marker detection method of detecting a radiopaque marker disposed in a probe on multiple X-ray images captured while the probe for acquiring a tomographic image moves in an axial direction of a catheter, the method comprising:

extracting a line extending along the probe from an X-ray image captured during a pre-pullback period before the probe starts to move; and detecting a position of a radiopaque marker disposed in the probe on each of the multiple X-ray images captured during the movement of the probe following the pre-pullback period, by using the line extracted.

20. A non-transitory computer readable storage medium that causes a processor to execute each process for the radiopaque marker detection method according to claim 19.

* * * * *